United States Patent [19]

Bergman

[11] Patent Number: 4,605,519

[45] Date of Patent: Aug. 12, 1986

[54] O- AND S-(2-MERCAPTOALKYL)- MONO- OR DIHYDROCARBYL CARBAMOTHIOATES AND S-(2-MERCAPTOALKYL)MONO- OR DIHYDROCARBYL CARBAMODITHIOATES

[75] Inventor: Roger W. Bergman, Midland, Mich.

[73] Assignee: The Dow Chemical Company, Midland, Mich.

[21] Appl. No.: 560,006

[22] Filed: Dec. 9, 1983

[51] Int. Cl.[4] .................... C07C 155/02; C07C 125/06

[52] U.S. Cl. .................................... 558/234; 560/165; 558/236; 558/239

[58] Field of Search .................... 260/455 A; 560/165

[56] References Cited

U.S. PATENT DOCUMENTS

| | | | |
|---|---|---|---|
| 3,579,516 | 5/1971 | Albert | 260/455 A |
| 3,728,371 | 5/1973 | Doyle, Jr. | 260/455 A |
| 4,298,524 | 11/1981 | Calcagno | 260/455 A |

FOREIGN PATENT DOCUMENTS

| | | | |
|---|---|---|---|
| 53979 | 9/1928 | Japan | 260/455 A |

*Primary Examiner*—Henry R. Jiles
*Assistant Examiner*—Robert C. Whittenbaugh

[57] ABSTRACT

The invention relates to novel O- or S-(2-mercaptoalkyl)mono- or dihydrocarbyl carbamothioates and S-(2-mercaptoalkyl)mono- or dihydrocarbyl carbamodithioate. The novel compounds of this invention are useful as collectors in the froth flotation of sulfide mineral ores.

19 Claims, No Drawings

O- AND S-(2-MERCAPTOALKYL)- MONO- OR DIHYDROCARBYL CARBAMOTHIOATES AND S-(2-MERCAPTOALKYL)MONO- OR DIHYDROCARBYL CARBAMODITHIOATES

BACKGROUND OF THE INVENTION

This invention relates to novel compounds, specifically O- or S-(2-mercaptoalkyl)mono- or dihydrocarbyl carbamothioates and S-(2-mercaptoalkyl)mono- or dihydrocarbyl carbamodithioates and their use as collectors in the recovery of sulfide ores by froth flotation.

Flotation is a process of treating a mixture of finely divided mineral solids, e.g., a pulverulent ore, suspended in a liquid whereby a portion of such solids is separated from other finely divided mineral solids, e.g., clays and the like materials present in the ore, by introducing a gas into the liquid (or providing a gas in situ) to produce a frothy mass containing certain of the solids on the top of the liquid, and leaving suspended (unfrothed) other solid components of the ore. Flotation is based on the principle that introducing a gas into a liquid containing solid particles of different materials suspended therein causes adherence of some gas to certain suspended solids and not to others and makes the particles having the gas thus adhered thereto lighter than the liquid. Accordingly, these particles rise to the top of the liquid to form a froth.

An understanding of the phenomena which makes flotation a particularly valuable industrial operation is not essential to the practice of the present invention. Such phenomena appear, however, to be largely associated with selective affinity of the surface of particulated solids, suspended in a liquid containing entrapped gas, for the liquid on one hand and the gas on the other.

The flotation principle is applied in a number of mineral separation processes among which is the selective separation of such minerals as sulfide copper minerals, sulfide zinc minerals, sulfide molybdenum minerals and others from sulfide iron minerals.

Various flotation agents have been admixed with the suspension to improve the frothing process. Such added agents are classed according to the function to be performed: collectors, e.g., high carbon chain compounds such as collectors for sulfide minerals including xanthates, thionocarbamate, dithiophosphates, mercaptans, and the like; frothers which impart the property of forming a stable froth, e.g., natural oils such as pine oil and eucalyptus oil; modifiers such as activators to induce flotation in the presence of a collector, e.g., copper sulfate, depressants, e.g., sodium cyanide, which tend to prevent a collector from functioning as such on a certain mineral which it is desired to retain in the liquid, and thereby discourage a substance from being carried up and forming a part of the froth; pH regulators to produce optimum metallurgical results, e.g., lime, soda ash and the like.

These foregoing flotation additaments are selected for use according to the nature of the ore, the mineral sought to be recovered, and the other additaments which are to be used in combination therewith.

Xanthates and dithiophosphates are relatively inexpensive collectors but have a comparatively low activity as collectors, thus requiring larger concentrations than some other collectors to get satisfactory activity. The thionocarbamates have good activity as collectors but are relatively expensive to produce. Further, in the preparation of thionocarbamates, salt and odorous by-products are prepared. These by-products must be removed from the thionocarbamates.

There is needed a froth flotation collector which is relatively inexpensive to prepare which has a high activity as a collector for sulfide ores. There is further needed a collector which can be prepared by a process that does not produce salt or odorous by-products.

SUMMARY OF THE INVENTION

The invention relates to novel O- or S-(2-mercaptoalkyl)mono- or dihydrocarbyl carbamothioates and S-(2-mercaptoalkyl)mono- or dihydrocarbyl carbamodithioates.

Another aspect of this invention is a process for the preparation of O- or S-(2-mercaptoalkyl)mono- or dihydrocarbyl carbamothioates and S-(2-mercaptoalkyl)-mono- or dihydrocarbyl carbamodithioates which comprises contacting a 1,3-oxathiolane-2-thione or a 1,3-dithiolone-2-thione with a primary or secondary amine in an organic solvent under conditions such that an S- or O-(2-mercaptoalkyl)mono- or dihydrocarbyl carbamothioate or an S-(2-mercaptoalkyl)mono- or dihydrocarbyl carbamodithioate is formed.

A further aspect of this invention is a process of concentrating sulfide ores by flotation, which comprises subjecting the sulfide ore in the form of a pulp, to a flotation process in the presence of a floating amount of a flotation collector for the sulfide comprising a O- or S-(2-mercaptoalkyl)mono- or dihydrocarbyl carbamothioate (hereinafter mercaptothioates) or S-(2-mercaptoalkyl)mono- or dihydrocarbyl carbamodithioate (hereinafter mercaptodithioates).

The mercaptothioates and mercaptodithioates of this invention have good activity as collectors. Further, the compounds of this invention are less expensive to prepare than the thionocarbamates. Also, the process for the preparation of the compounds of this invention does not result in the preparation of salt.

DETAILED DESCRIPTION OF THE INVENTION

Preferred O- or S-(2-mercaptoalkyl)mono- or dihydrocarbyl carbamothioates and S-(2-mercaptoalkyl)-mono- or dihydrocarbyl carbamodithioates include compounds which correspond to the formula

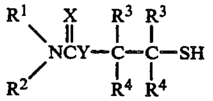

wherein $R^1$ is hydrogen or $C_{1-20}$ hydrocarbyl;

$R^2$ is $C_{1-20}$ hydrocarbyl;

$R^3$ is separately in each occurrence hydrogen or $C_{1-20}$ hydrocarbyl;

$R^4$ is separately in each occurrence hydrogen or $C_{1-20}$ hydrocarbyl;

X is O or S; and

Y is O or S;

with the proviso that both X and Y cannot be oxygen and with the further proviso that at least one $R^3$ and one $R^4$ on the same carbon atom on the alkylene moiety must be hydrogen.

Preferred O-(2-mercaptoalkyl)mono- or dihydrocarbyl carbamothioates) of this invention include those corresponding to the formula

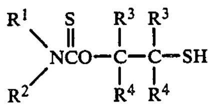

wherein $R^1$, $R^2$, $R^3$ and $R^4$ are as defined above. Preferred S-(2-mercaptoalkyl)mono- or dihydrocarbyl carbamothioates of this invention include those compounds which correspond to the formula

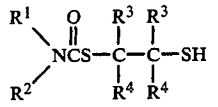

wherein $R^1$, $R^2$, $R^3$ and $R^4$ are as defined above.

Preferred S-(2-mercaptoalkyl)mono- or dihydrocarbyl carbamodithioates of this invention include those corresponding to the formula

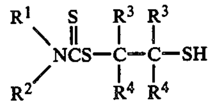

wherein $R^1$, $R^2$, $R^3$ and $R^4$ are as defined above.

$R^1$ is preferably hydrogen or $C_{1-20}$ alkyl and most preferably hydrogen. $R^2$ is preferably $C_{1-20}$ alkyl or phenyl; more preferably $C_{2-10}$ alkyl, and most preferably $C_{2-6}$ alkyl. $R^3$ is preferably hydrogen or $C_{1-20}$ alkyl, more preferably hydrogen or $C_{1-4}$ alkyl, and most preferably hydrogen. $R^4$ is preferably $C_{1-20}$ alkyl and most preferably $C_{1-4}$ alkyl.

In one preferred embodiment, the nitrogen atom on the carbamate moiety is substituted with one hydrocarbyl group. In another preferred embodiment, the alkylene moiety has only one substituent.

$C_{1-20}$ hydrocarbyl means herein an organic radical containing between one and twenty carbon atoms to which are bonded hydrogen atoms. Included are the following groups: $C_{1-20}$ alkyl, $C_{1-20}$ alkenyl, $C_{1-20}$ alkynyl, $C_{3-20}$ cycloalkyl, $C_{3-20}$ cycloalkenyl, $C_{6-20}$ aryl, $C_{7-20}$ alkaryl or $C_{7-20}$ aralkyl.

The term aryl refers herein to biaryl, phenyl, naphthyl, phenanthranyl and anthranyl. Alkaryl refers herein to an alkyl-, alkenyl- or alkynyl-substituted aryl substituent wherein aryl is as defined hereinbefore. Aralkyl means herein an alkyl, alkenyl or alkynyl substituent substituted with an aryl group, wherein aryl is as defined hereinbefore.

$C_{3-20}$ cycloalkyl refers to an alkyl group containing one, two, three or more cyclic rings. $C_{3-20}$ cycloalkenyl refers to mono-, di- and polycyclic groups containing one or more double bonds. $C_{3-20}$ cycloalkenyl also refers to the cycloalkenyl groups wherein two or more double bonds are present.

The O- or S-(2-mercaptoalkyl)mono- or dihydrocarbyl carbamothioates are prepared by reacting a primary or secondary amine with a 1,3-oxathiolane-2-thione in a suitable solvent to prepare a S-(2-mercaptoalkyl)mono- or dihydrocarbyl carbamothioate, O-(2-mercaptoalkyl)-mono- or dihydrocarbyl carbamothioate, or mixtures thereof.

The S-(2-mercaptoalkyl)mono- or dihydrocarbyl carbamodithioates are prepared by contacting a 1,3-dithiolane-2-thione with a primary or secondary amine to prepare a (2-mercaptoalkyl)mono- or dihydrocarbyl carbamodithioate.

Amines useful in this process include those which correspond to the formula $HNR^1R^2$ wherein $R^1$ and $R^2$ are as defined hereinbefore.

Specific illustrative examples of the amines contemplated herein are shown by the following:

(1) monoalkylamines including methylamine, ethylamine, propylamine, isopropylamine, n-butylamine, sec-butylamine, isobutylamine, pentylamines, hexylamines, cyclohexylamines, heptylamines, octylamines, dodecylamines, octadecylamines, eicosylamines, triacontanylamines, benzylamine, chlorobenzylamine, nitrobenzylamine, 2-ethoxyethylamine, 4-carbomethoxyhexylamine, etc.;

(2) dialkylamines including dimethylamine, diethylamine, di-n-propylamine, diisopropylamine, di-n-butylamine, di-sec-butylamine, diisobutylamine, di-tert-butylamine, dipentylamines, dihexylamines, dioctylamines, ditriacontanylamine, N-methylethylamine, N-methylpropylamine, N-methyloctadecylamine, N-ethylhexylamine, N-ethyldodecylamine, N-propyldodecylamine, etc.;

(3) heterocyclic aliphatic secondary amines including piperazine, pyrrole, imidazoline, pyrazole, piperazine, etc;

(4) arylamines including aniline, toluidine, anisidine, nitroaniline, bromoaniline, xylidines, 4-ethylaniline, naphthylamine, etc.;

(5) diarylamines including diphenylamine, N-phenyl-2-naphthylamine, N-phenylnaphthylamine, etc.;

(6) alkylarylamines having from 1 to about 30 carbon atoms in the alkyl group attached either to the nitrogen atom or to the aryl group including N-ethylaniline, N-methyl-o-toluidine, N-methyl-p-toluidine, p-chloro-N-methylaniline, N,N'-dimethylphenylenediamine, 4-ethylaniline, 4-propylaniline, 4-butylaniline, 4-decylaniline, etc.; and (7) aminoalkyl-substituted amines including ethylenediamine, diethylenetriamine, triethylenetetramine, 1,3-propylenediamine, di-1,3-propylenetriamine, 1,6,11,16-tetraazahexadecane.

The 1,3-oxathiolane-2-thiones useful in this invention include those corresponding to the formula

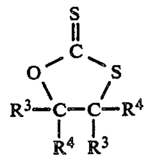

wherein $R^3$ and $R^4$ are as defined hereinbefore, with the proviso that the $R^3$ and $R^4$ attached to one of the carbon atoms must be hydrogen, that is either the 4 carbon or the 5 carbon must be unsubstituted. Included are 1,3-oxathiolane-2-thione, 5-methyl-1,3-oxathiolane-2-thione, 5-ethyl-1,3-oxathiolane-3-thione, 5-propyl-1,3-oxathiolane-2-thione, 5-butyl-1,3-oxathiolane-2-thione, 5-pentyl-1,3-oxathiolane-2-thione, 5,5-dimethyl-1,3-oxathiolane-2-thione, 5,5-diethyl-1,3-oxathiolane-2-thione, 5,5-dipropyl-1,3-oxathiolane-2-thione, 5,5-dibutyl-1,3-oxathiolane-2-thione, 5,5-dipentyl-1,3-oxathiolane-2-thione, 5-phenyl-1,3-oxathiolane-2-thione. The 1,3-oxathiolane-2-thiones can be prepared by the method taught in U.S. Pat. No. 3,409,635 (incorporated herein by reference).

The 1,3-dithiolane-2-thiones useful in this invention correspond to the formula

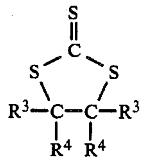

wherein $R^3$ and $R^4$ are as defined above and with the proviso that the $R^3$ and $R^4$ attached to one of the carbon atoms must be hydrogen, that is either the 4 carbon or the 5 carbon must be unsubstituted. 1,3-Dithiolane-2-thiones are prepared by contacting carbon disulfide with an alkylene episulfide at a temperature of between 10° C. and 80° C. in the presence of a catalyst comprising an alkali metal hydroxide or alkali metal alkoxide, 2 to 12 weight percent water based on the alkali metal hydroxide or alkali metal alkoxide, and an alkylsulfonium halide or methanol.

In the preparation of a S- or O-(2-mercaptoalkyl)-mono- or dihydrocarbyl carbamothioate or (2-mercaptoalkyl)mono- or dihydrocarbyl carbamodithioate, an amine and a 1,3-oxathiolane-2-thione or 1,3-dithiolane-2-thione are contacted in a suitable solvent. Preferably in a molar ratio of between about 0.95:1.0 to 1.0:1.0 of 1,3-oxathiolane-2-thione or 1,3-dithiolane-2-thione to amine, more preferably in a 1:1 molar ratio. Although excesses of either reagent are within the scope of this invention, the reactants react in a stoichiometric manner such that the use of such an excess provides no significant advantage.

Suitable solvents include any inert organic solvent which dissolves the reactants. Preferred solvents are nonpolar organic solvents. Nonpolar organic solvents include aromatic hydrocarbons, aliphatic hydrocarbons, chlorinated aromatic hydrocarbons, aliphatic chlorinated hydrocarbons, cyclic ethers and aliphatic ethers. Examples of aromatic solvents include benzene, toluene, xylene, ethylbenzene and the like. Examples of aliphatic hydrocarbons include hexane, heptane, octane and the like. Examples of chlorinated aromatic hydrocarbons include monochlorobenzenes, dichlorobenzenes, trichlorobenzenes, monochlorotoluene, monochloroethylbenzene and the like. Chlorinated aliphatic hydrocarbons include chloromethane, dichloromethane, trichloromethane, tetrachloromethane, chloroethane, dichloroethane, 1,1,1-trichloroethane, vinyl chloride, vinylidene chloride and the like. Cyclic ethers include tetrahydrofuran and the like. Aliphatic ethers include ethyl ether and the like.

Preferred solvents are cyclic ethers and aliphatic ethers, with tetrahydrofuran most preferred.

This process can be run at any temperature at which the reaction rate is reasonable and the product is acceptable. Preferred temperatures are between about −40° C. and 30° C., with between about 0° C. and 20° C. more preferred and between about 0° C. and 10° C. most preferred. Below −40° C. the reaction rate is low, above 30° C. a significant amount of dialkylthiourea by-products is prepared.

The reaction time is generally between about 1 minute and several hours with between about 30 and 120 minutes being preferred.

The mercaptothioates and mercaptodithioates are generally recovered by removing the solvents, for example, by stripping off the solvents on a rotary evaporator.

When a 1,3-oxathiolane-2-thione is the initial starting material, the product generally comprises a mixture of the O-(2-mercaptoalkyl)mono- or dihydrocarbyl carbamothioate and S-(2-mercaptoalkyl)mono- or dihydrocarbyl carbamothioates. The O-(2-mercaptoalkyl)-mono- or dihydrocarbyl carbamothioates are preferred as they are better sulfide ore collectors. The ratio of the O-(2-mercaptoalkyl)mono- or dihydrocarbyl carbamothioates to the S-(2-mercaptoalkyl)mono- or dihydrocarbyl carbamothioates can be increased by running the reaction at lower temperatures and using shorter reaction times. The O-(2-mercaptoalkyl)mono- or dihydrocarbyl carbamothioates are thermally less stable than the S-(2-mercaptoalkyl)mono- or dihydrocarbyl carbamothioates and at higher temperatures undergo rearrangement to the latter compounds.

In one preferred embodiment the process described herein is performed as follows. The 1,3-oxathiolane-2-thione is dissolved in an organic solvent (i.e., tetrahydrofuran, dichloromethane or toluene). The solution is cooled to between 0° C. and 25° C. A quantitative amount of amine is added slowly, while the temperature is maintained at between about 0° C. and 25° C. The reaction is allowed to go to completion (generally between 0.5 and 2.0 hours). The solvent is removed to obtain the crude product.

The O-(2-mercaptoalkyl)mono- or dihydrocarbyl carbamothioates, S-(2-mercaptoalkyl)mono- or dihydrocarbyl carbamothioates and S-(2-mercaptoalkyl)-mono- or dihydrocarbyl carbamodithioates are useful as collectors for sulfide ores in froth flotation processes. Generally, the compounds are added to a frothing aqueous sulfide ore pulp in which they aid the sulfide ores in becoming attached to the air bubbles and being carried with the bubbles into the froth.

Sulfide ores for which these compounds are useful include copper sulfide-, zinc sulfide-, molybdenum sulfide-, cobalt sulfide-, nickel sulfide-, lead sulfide-, arsenic sulfide-, silver sulfide-, chromium sulfide-, gold sulfide-, platinum sulfide- and uranium sulfide-containing ores. It is preferable to use the O-(2-mercaptoalkyl)-mono- or dihydrocarbyl carbamothioates and (2-mercaptoalkyl)mono- or dihydrocarbyl carbamodithioates as collectors for copper sulfide ores. Examples of sulfide ores from which metal sulfides may be concentrated by froth flotation using the O-(2-mercaptoalkyl)mono- or dihydrocarbyl carbamothioates and (2-mercaptoalkyl)-mono- or dihydrocarbyl carbamodithioates of this invention as collectors include copper-bearing ores such as, for example, corvallite ($CuS$), chalcocite ($Cu_2S$), chalcopyrite ($CuFeS_2$), bornite ($Cu_5FeS_4$), cubanite ($Cu_2SFe_4S_5$), valerite ($Cu_2Fe_4S_7$ or $Cu_3Fe_4S_7$), enargite ($Cu_3(AsSb)S_4$), tetrahedrite ($Cu_3SbS_2$), tennanite ($Cu_{12}As_4S_{13}$), cuprite ($Cu_2O$), tenorite ($CuO$), malachite ($Cu_2(OH)_2CO_3$), azurite ($Cu_3(OH)_2CO_3$), antlerite ($Cu_3SO_4(OH)_4$), brochantite ($Cu_4(OH)_6SO_4$), atacamite ($Cu_2Cl(OH)_3$), chrysocolla ($CuSiO_7$), famatinite ($Cu_3(SbAs)S_4$), and bournonite ($PbCuSbS_3$); lead-bearing ores such as, for example, Galena ($PbS$); antimony-bearing ores such as, for example, stilnite ($Sb_2S_4$); zinc-bearing ores such as, for example, sphalerite ($ZnS$), zincite ($ZnO$), and smithsonite ($ZnCO_3$); silver-bearing ores such as, for example, argentite ($Ag_2S$), stephanite ($Ag_5SbS_4$), and hessite ($AgTe_2$); chromium-bearing ores such as, for example, daubreelite ($FeSCrS_3$) and chromite ($FeOCr_2O_3$); gold-bearing ores such as, for example, sylvanite ($AuAgTe_2$) and calaverite (AuTe); platinum-bearing ores such as, for example, cooperite ($Pt(AsS)_2$) and sperrylite ($PtAs_2$); and uranium-bearing ores such as, for example, pitchblende ($U_2O_5(U_3O_8)$ and gummite ($UO_3nH_2O$).

The amount of the mercaptothioate or mercaptodithioate used for froth flotation depends upon the type of ore used, the grade of the ore, the size of the ore particles and the particular compound used. Generally, that amount which separates the desired metal sulfide from the sulfide ore is suitable. Preferably between about 0.005 and 0.25 lb of mercaptothioates or mercaptodithioates per ton of ore, most preferably between about 0.015 and 0.08 lb per ton of ore is used.

Mixtures of O-(2-mercaptoalkyl)mono- or dihydrocarbyl carbamothioates and S-(2-mercaptoalkyl)mono- or dihydrocarbyl carbamothioates are usually used in froth flotation of sulfide ores, because the process described hereinbefore prepares mixtures of the compounds. Each of the species can be used alone for froth flotation of sulfide ores. O-(2-mercaptoalkyl)mono- or dihydrocarbyl carbamothioates and S-(2-mercaptoalkyl)mono- or dihydrocarbyl carbamothioates are the preferred species as they are generally better collectors, with the O-(2-mercaptoalkyl)mono- or dihydrocarbyl carbamothioates being most preferred.

The froth flotation processes in which the mercaptothioates or mercaptodithioates of this invention are used, are those which are well-known in the art. In most of these processes, use of frothing agents is required. It is contemplated that the mercaptothioates or mercaptodithioates of this invention will be used along with frothers. Further, the collectors of this invention can be used in mixtures with other known collectors.

In one preferred embodiment, the collectors of this invention are used with a surfactant which emulsifies the collectors in aqueous solution. Generally, useful collectors include nonionic surfactants and anionic surfactants wherein the anionic surfactants are soluble in the collector. It is preferable that the surfactants used have a hydrophilic-lipophilic balance (HLb) of between about 8 and 12. Between about 0.01 and 40 weight percent of surfactant based upon the collector is used. The collector and surfactant are generally contacted before contacting the mixture with aqueous froth flotation medium.

Included among anionic surfactants useful in this invention are those disclosed in Kirk-Othmer *Encyclopedia of Chemical Technology,* 3d Ed. 22, 347–360 (1983) (incorporated herein by reference). Examples of anionic surfactants include polyalkoxycarboxylates, N-acylsaccosinates, acylated protein hydrolysates, alkylbenzenesulfonates, alkylarenesulfonates, α-olefinsulfonates, lignosulfonates, napthalenesulfonates, petroleum sulfonates, dialkylsulfonates, amidosulfonates, 2-sulfoethyl esters of fatty acids, alcohol sulfates and phosphate esters.

Included among nonionic surfactants useful in this invention are those described in Kirk-Othmer *Encyclopedia of Chemical Technology* 3d. Ed., 23, 360–377 (1983) (incorporated herein by reference). Examples of nonionic surfactants include polyoxy ethylene adducts of alcohols, polyoxyalkyene adducts of phenols, polyoxyalkylene adducts of alkyl substituted phenols, glycerol esters, anhydrosorbitol esters, ethoxylated anhydrosorbitol esters, glycerol esters of fatty acids, carboxylic amides, diethanol fatty acid condensates, monoalkanolamine fatty acid condensates, polyoxyethylene fatty acid amides, and polyalkyleneoxide block copolymers.

Preferred nonionic surfactants are polyoxyethylene adducts of alcohols, polyoxyethylene adducts of phenols, and polyoxyethylene adducts of alkylphenols. More preferred are polyoxyethylene adducts of alcohols, with tetraethyleneglycol adducts of lauryl alcohol being most preferred.

Numerous collectors are known in flotation practice or have been proposed in the technical and patent literature. Generic examples include xanthates, thiocarbamates, dithiophosphates, thiocarbanilide, xanthogen formates, alkylamines, quaternary ammonium compounds, sulfonates and the like. Any collector which is known in the art as suitable for the beneficiation by flotation of sulfide mineral ores can be used in this invention. Further blends of known collectors can also be used in this invention.

Suitable frothers include some compounds which are also useful as collectors such as fatty acids, soaps, and alkyl aryl sulfonates, but the best frothers are those which have a minimum of collecting properties. They are polar-nonpolar molecules of the type $C_5H_{11}OH$, amyl alcohol or $C_{10}H_{17}OH$, the active constituent of the well-known frother pine oil. The aliphatic alcohols used as frothers preferably have chain lengths of 5 to 8 carbon atoms, provided there is sufficient branching in the chain. Alcohols in the 10 to 12 carbon atom range are good frothers. Other examples include polyalkylene glycols, polyoxyalkylene paraffins and cresylic acids. Blends of frothers may also be used. All frothers which are suitable for beneficiation of sulfide mineral ores by froth flotation can be used in this invention.

The mercaptothioate and mercaptodithioate collectors of this invention demonstrate good recoveries and rates of recovery.

SPECIFIC EMBODIMENTS

The following examples are included for illustration and do not limit the scope of the invention or claims. Unless otherwise indicated, all parts and percentages are by weight.

In the following examples, the performance of the frothing processes described is shown by giving the rate constant of flotation and the amount of recovery at infinite time. These numbers are calculated by using the formula $$\gamma = R_\infty \left[ 1 - \frac{1 - e^{-kt}}{kt} \right]$$

wherein: γ is the amount of mineral recovered at time t, k is the rate constant for the rate of recovery and $R_\infty$ is the calculated amount of the mineral which would be recovered at infinite time. The amount recovered at various times is determined experimentally and the series of values are substituted into the equation to obtain the $R_\infty$ and k. The above formula is explained in Klimpel, "Selection of Chemical Reagents for Flotation", Ch. 45, pp. 907–934, *Mineral Processing Plant Design,* 2d Ed., Eds. Mular and Bhappu, published by Society of Mining Engineers, N.Y. (1980) (incorporated herein by reference).

EXAMPLES 1-5

Flotation of Copper Sulfide Ores

Three of the O- or S-(2-mercaptoalkyl)mono- or dihydrocarbyl carbamothioates and S-(2-mercaptoalkyl)-mono- or dihydrocarbyl carbamodithioates of this invention and prior art collectors are used for the flotation of copper sulfide. The procedure for such flotation is described hereinafter. The results are compiled in Table I.

Procedure

The flotation cell used is a 6.5×6.5×8-inch plexiglass container which holds approximately 2.8 liters of deionized water, ore, collector and frother. A rotating paddle is provided for skimming the frother from the top of the cell. An air inlet is placed in the bottom of the cell.

A copper sulfide ore from the Inspiration Consolidated Copper Company is preground to −10 mesh. Immediately before floating the ore is ground in a rod mill for an additional period of time to obtain the desired mesh size. The process of this grinding is as follows. Eight rods of one inch each are put in a rod mill along with 1000 g of ore, 0.6 g of lime (to bring the pH to 10.6), 600 g of deionized water, 0.05 lb of collector per ton of ore (0.025 g), and the mixture is ground at 60 rpm for about 25 minutes, until approximately 80 percent of the particles had a size of less than 200 mesh.

Thereafter, the slurry is transferred to the float cell as described hereinbefore. The frother, Dowfroth ®1012 (a polypropylene glycol ether available from The Dow Chemical Company, Midland, Mich.) is added to the cell, 0.08 lb per ton of ore (0.04 g). Deionized water is added to bring the water up to the desired level in the float cell. The mixture in the float cell is stirred at 900 rpm for 2 minutes to condition the ore. After 2 minutes of stirring, the air flow of 9 liters/minute is started, with continued stirring, and a paddle rotation of 10 rpm is started. Further water is added to maintain the water level. The froth from the cell is skimmed by the paddle into a collection tray. The froth skimmed off is collected at intervals of 0.5, 1.5, 3.0, 5.0 and 8.0 minutes. Each sample is dried overnight in a forced air oven at 95° C.

The samples are weighed and analyzed for copper content by plasma emission spectroscopy.

The recovery and rate are calculated from the copper content and time of each sample using the equation described hereinbefore.

The procedure for the analysis by plasma emission spectroscopy is as follows. Into a 100-cc flask is placed 0.2 to 0.25 g of ore sample (approximately 2.0 g if it is a tailings sample, the ore left in the cell after flotation). To this is added 3.5 cc of concentrated hydrochloric acid and 5.0 cc of concentrated nitric acid. The mixture is heated to boiling and boiled for 25 minutes, and then allowed to cool. To this is added 25 cc of deionized water. The mixture is heated to boiling then allowed to cool. The mixture is filled to the volumetric line. A plasma emission spectrometer (Spectrospan IV) is used to determine the copper level in the solutions prepared. The copper emission line at 2135.98 nm is found to give a linear response with copper concentration. The instrument is standardized by the use of copper solution standards. When the sample solution is aspirated into the plasma, the concentration in ppm of Cu is shown by the instrument by digital display. This ppm of Cu is converted into percent Cu in the original sample by the following equation:

$$\% \text{ Cu in original sample} = \frac{(\text{ppm Cu})(10^{-6})(100)}{(\text{grams of sample used})} \times 100\%.$$

The results are compiled in Table I.

TABLE I

| | | Copper | | Gangue | |
|---|---|---|---|---|---|
| Example | CCompound | R | K | R | K |
| 1* | Blank | 0.16 | 2.7 | 0.032 | 4.5 |
| 2* | Z-11** | 0.55 | 4.3 | 0.032 | 3.7 |
| 3 | 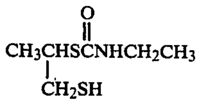 | 0.48 | 4.3 | 0.054 | 4.1 |
| 4 | 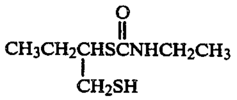 | 0.65 | 4.4 | 0.044 | 3.6 |
| 5 | 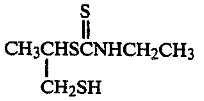 | 0.25 | 3.0 | 0.054 | 3.3 |

*Not an example of this invention.

**Z-11 is 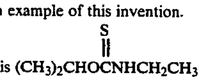

The examples demonstrate that the compounds of this invention demonstrate activity as collectors for sulfide ores. Furthermore, some of these compounds demonstrate rates and recoveries comparable to commercial collectors.

What is claimed is:

1. A 2-mercaptoalkyl carbamothioate which corresponds to the formula:

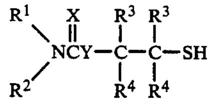

wherein $R^1$ is hydrogen or $C_{1-20}$ hydrocarbyl;

$R^2$ is $C_{1-20}$ hydrocarbyl;

$R^3$ is separately in each occurrence hydrogen or $C_{1-20}$ hydrocarbyl;

$R^4$ is separately in each occurrence hydrogen or $C_{1-20}$ hydrocarbyl;

X is O or S; and

Y is O or S;

with the proviso that both X and Y cannot be oxygen and with the further proviso that at least one $R^3$ and one $R^4$ on the same carbon atom on each alkylene moiety must be hydrogen.

2. The O-(2-mercaptoalkyl)mono- or dihydrocarbyl carbamothioate of claim 1 which corresponds to the formula

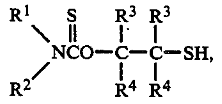

wherein $R^1$, $R^2$, $R^3$ and $R^4$ are as defined in claim 1.

3. The S-(2-mercaptoalkyl)mono- or dihydrocarbyl carbamothioate of claim 1 which corresponds to the formula

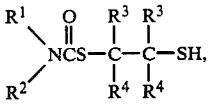

wherein $R^1$, $R^2$, $R^3$ and $R^4$ are as defined in claim 1.

4. The (2-mercaptoalkyl)mono- or dihydrocarbyl carbamodithioate of claim 1 which corresponds to the formula

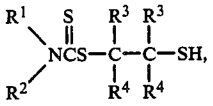

wherein $R^1$, $R^2$, $R^3$ and $R^4$ are as defined in claim 1.

5. The mercaptothioates or mercaptodithioates of claim 2, 3 or 4 wherein $R^1$ is hydrogen or $C_{1-20}$ alkyl.

6. The mercaptothioates or mercaptodithioates of claim 5 wherein $R^1$ is hydrogen.

7. The mercaptothioates or mercaptodithioates of claim 6 wherein $R^2$ is $C_{1-20}$ alkyl or phenyl.

8. The mercaptothioates or mercaptodithioates of claim 7 wherein $R^2$ is $C_{2-10}$ alkyl.

9. The mercaptothioates or mercaptodithioates of claim 8 wherein $R^2$ is $C_{2-6}$ alkyl.

10. The mercaptothioates or mercaptodithioates of claim 5 wherein $R^3$ is hydrogen or $C_{1-20}$ alkyl and $R^4$ is $C_{1-20}$ alkyl.

11. The mercaptothioates or mercaptodithioates of claim 10 wherein $R^3$ is hydrogen or $C_{1-4}$ alkyl and $R^4$ is $C_{1-4}$ alkyl.

12. The mercaptothioates or mercaptodithioates of claim 11 wherein $R^3$ is hydrogen and $R^4$ is $C_{1-4}$ alkyl.

13. A process for the preparation of O-(2-mercaptoalkyl)mono- or dihydrocarbyl carbamothioates, S-(2-mercaptoalkyl)mono- or dihydrocarbyl carbamothioates, or (2-mercaptoalkyl)mono- or dihydrocarbyl carbamodithioates which comprises contacting a 1,3-oxathiolane-2-thione or 1,3-dithiolane-2-thiones with a primary or secondary amine in an organic solvent under conditions such that an O- or S-(2-mercaptoalkyl)mono- or dihydrocarbyl carbamothioate or (2-mercaptoalkyl)-mono- or dihydrocarbyl carbamodithioate is formed.

14. The process of claim 13 wherein the amine corresponds to the formula $NHR^1R^2$, the 1,3-oxathiolane-2-thione corresponds to the formula

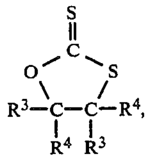

wherein the 1,3-dithiolane-2-thione corresponds to the formula

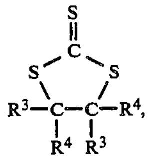

wherein $R^1$ is hydrogen or $C_{1-20}$ hydrocarbyl;

$R^2$ is hydrogen or $C_{1-20}$ hydrocarbyl;

$R^3$ is separately in each occurrence hydrogen or $C_{1-20}$ hydrocarbyl; and $R^4$ is separately in each occurrence hydrogen or $C_{1-20}$ hydrocarbyl, with the proviso that at least one $R^3$ and $R^4$ on the same carbon atom on each alkylene moiety must be hydrogen.

15. The process of claim 14 wherein the temperature is between about −40° C. and 30° C.

16. The process of claim 15 wherein the temperature is between about 0° C. and 20° C.

17. The process of claim 16 wherein the solvent is an aromatic hydrocarbon, a chlorinated aliphatic hydrocarbon, a chlorinated aromatic hydrocarbon, or aliphatic ether or a cyclic ether.

18. The process of claim 17 wherein the solvent is an aliphatic ether or a cyclic ether.

19. The process of claim 18 wherein the solvent is tetrahydrofuran.

* * * * *